United States Patent
Spratt et al.

(10) Patent No.: US 10,238,441 B2
(45) Date of Patent: Mar. 26, 2019

(54) BOTTOM-LOADING BONE ANCHOR ASSEMBLIES AND METHODS

(71) Applicant: Medos International Sarl, Le Locle (CH)

(72) Inventors: Frank Spratt, Middleboro, MA (US); Thibault Chandanson, Villers le lac (FR); Ernest Quintanilha, Norton, MA (US); Shawn D. Stad, Lakeville, MA (US); Ralf Klabunde, Winterthur (CH)

(73) Assignee: Medos International Sàrl, Le Locle (CH)

( * ) Notice: Subject to any disclaimer, the term of this patent is extended or adjusted under 35 U.S.C. 154(b) by 0 days.

(21) Appl. No.: 15/692,822

(22) Filed: Aug. 31, 2017

(65) Prior Publication Data
US 2017/0360491 A1    Dec. 21, 2017

Related U.S. Application Data

(63) Continuation of application No. 13/828,882, filed on Mar. 14, 2013, now Pat. No. 9,775,660.

(51) Int. Cl.
*A61B 17/70* (2006.01)
*A61B 17/86* (2006.01)

(52) U.S. Cl.
CPC ...... *A61B 17/8685* (2013.01); *A61B 17/7037* (2013.01)

(58) Field of Classification Search
USPC .................. 606/266, 268, 269; 411/380, 396
See application file for complete search history.

(56) References Cited

U.S. PATENT DOCUMENTS

| | | | |
|---|---|---|---|
| 2,509,081 A | * | 5/1950 | Bluth ...................... F16B 21/18 403/375 |
| 2,788,045 A | | 4/1957 | Rosan |
| 2,842,180 A | | 7/1958 | Brown et al. |
| 4,124,318 A | | 11/1978 | Sagady |
| 4,762,024 A | | 8/1988 | Graft |

(Continued)

FOREIGN PATENT DOCUMENTS

| | | |
|---|---|---|
| DE | 299 03 342 U1 | 6/1999 |
| EP | 0 470 660 B1 | 2/1992 |

(Continued)

OTHER PUBLICATIONS

[No Author Listed] A New Angle on Correction. Expedium. DePuy. 2009. 2 pages.

(Continued)

*Primary Examiner* — Jan Christopher Merene
(74) *Attorney, Agent, or Firm* — Nutter McClennen & Fish LLP; Derek Roller

(57) ABSTRACT

Bone anchor assemblies and methods are provided having a multi-component bone anchor that is configured to allow the shank of the bone anchor to be bottom loaded into a receiver member. In one embodiment, a bone anchor assembly is provided having a shank with a distal threaded portion and a proximal head portion, a ball having a spherical exterior surface and a central lumen sized to receive the head portion of the shank, and a clip configured to be engaged between the head portion and the ball such that the clip is effective to lock the ball in engagement with the shank.

19 Claims, 12 Drawing Sheets

(56) References Cited

U.S. PATENT DOCUMENTS

| | | |
|---|---|---|
| 5,009,017 A | 4/1991 | Diekevers et al. |
| 5,129,388 A | 7/1992 | Vignaud et al. |
| 5,154,719 A | 10/1992 | Cotrel |
| 5,306,275 A | 4/1994 | Bryan |
| 5,360,431 A | 11/1994 | Puno et al. |
| 5,385,565 A | 1/1995 | Ray |
| 5,443,467 A | 8/1995 | Biedermann et al. |
| 5,474,555 A | 12/1995 | Puno et al. |
| 5,486,174 A | 1/1996 | Fournet-Fayard et al. |
| 5,487,744 A | 1/1996 | Howland |
| 5,501,684 A | 3/1996 | Schlapfer et al. |
| 5,520,689 A | 5/1996 | Schlapfer et al. |
| 5,562,661 A | 10/1996 | Yoshimi et al. |
| 5,580,246 A | 12/1996 | Fried et al. |
| 5,643,260 A | 7/1997 | Doherty |
| 5,672,176 A | 9/1997 | Biedermann et al. |
| 5,782,833 A | 7/1998 | Haider |
| 5,797,911 A | 8/1998 | Sherman et al. |
| 5,879,350 A | 3/1999 | Sherman et al. |
| 5,885,286 A | 3/1999 | Sherman et al. |
| 5,941,882 A | 8/1999 | Jammet et al. |
| 5,964,591 A | 10/1999 | Beaty et al. |
| 5,989,250 A | 11/1999 | Wagner et al. |
| 6,050,997 A | 4/2000 | Mullane |
| 6,053,917 A | 4/2000 | Sherman et al. |
| 6,056,753 A | 5/2000 | Jackson |
| 6,068,632 A | 5/2000 | Carchidi et al. |
| 6,074,391 A | 6/2000 | Metz-Stavenhagen et al. |
| 6,077,262 A | 6/2000 | Schlapfer et al. |
| 6,090,111 A | 7/2000 | Nichols |
| 6,113,601 A | 9/2000 | Tatar |
| 6,146,383 A | 11/2000 | Studer et al. |
| 6,224,596 B1 | 5/2001 | Jackson |
| 6,224,598 B1 | 5/2001 | Jackson |
| 6,251,112 B1 | 6/2001 | Jackson |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,296,642 B1 | 10/2001 | Morrison et al. |
| 6,302,888 B1 | 10/2001 | Mellinger et al. |
| 6,355,038 B1 | 3/2002 | Pisharodi |
| 6,361,535 B2 | 3/2002 | Jackson |
| 6,379,356 B1 | 4/2002 | Jackson |
| 6,402,757 B1 | 6/2002 | Moore, III et al. |
| 6,440,132 B1 | 8/2002 | Jackson |
| 6,454,768 B1 | 9/2002 | Jackson |
| 6,454,772 B1 | 9/2002 | Jackson |
| 6,458,132 B2 | 10/2002 | Choi et al. |
| 6,475,218 B2 | 11/2002 | Goumay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,565,567 B1 | 5/2003 | Haider |
| 6,629,977 B1 | 10/2003 | Wolf |
| 6,660,004 B2 | 12/2003 | Barker et al. |
| 6,663,656 B2 | 12/2003 | Schmieding et al. |
| 6,723,100 B2 | 4/2004 | Biedermann et al. |
| 6,726,480 B1 | 4/2004 | Sutter |
| 6,726,687 B2 | 4/2004 | Jackson |
| 6,730,089 B2 | 5/2004 | Jackson |
| 6,736,820 B2 | 5/2004 | Biedermann et al. |
| 6,740,086 B2 | 5/2004 | Richelsoph |
| 6,755,836 B1 | 6/2004 | Lewis |
| 6,835,196 B2 | 12/2004 | Biedermann et al. |
| 6,843,790 B2 | 1/2005 | Ferree |
| 6,869,433 B2 | 3/2005 | Glascott |
| 6,884,244 B1 | 4/2005 | Jackson |
| 6,974,460 B2 | 12/2005 | Carbone et al. |
| 6,981,973 B2 | 1/2006 | McKinley |
| 6,997,927 B2 | 2/2006 | Jackson |
| 7,018,378 B2 | 3/2006 | Biedermann et al. |
| 7,022,122 B2 | 4/2006 | Amrein et al. |
| 7,083,621 B2 | 8/2006 | Shaolian et al. |
| 7,087,057 B2 | 8/2006 | Konieczynski et al. |
| 7,179,261 B2 | 2/2007 | Sicvol et al. |
| 7,186,255 B2 | 3/2007 | Baynham et al. |
| 7,198,625 B1 | 4/2007 | Hui et al. |
| 7,211,086 B2 | 5/2007 | Biedermann et al. |
| 7,223,268 B2 | 5/2007 | Biedermann |
| 7,235,075 B2 | 6/2007 | Metz-Stavenhagen |
| 7,261,716 B2 | 8/2007 | Strobel et al. |
| 7,264,621 B2 | 9/2007 | Coates et al. |
| 7,291,153 B2 | 11/2007 | Glascott |
| 7,322,981 B2 | 1/2008 | Jackson |
| 7,325,470 B2 | 2/2008 | Kay et al. |
| 7,445,627 B2 | 11/2008 | Hawkes et al. |
| 7,473,267 B2 | 1/2009 | Nguyen et al. |
| 7,559,943 B2 | 7/2009 | Mujwid |
| 7,572,279 B2 | 8/2009 | Jackson |
| 7,591,839 B2 | 9/2009 | Biedermann et al. |
| 7,604,655 B2 | 10/2009 | Warnick |
| 7,615,068 B2 | 11/2009 | Timm et al. |
| 7,625,394 B2 | 12/2009 | Molz, IV et al. |
| 7,670,362 B2 | 3/2010 | Zergiebel |
| 7,674,277 B2 | 3/2010 | Burd et al. |
| 7,678,137 B2 | 3/2010 | Butler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,699,876 B2 | 4/2010 | Barry et al. |
| 7,717,942 B2 | 5/2010 | Schumacher |
| 7,722,649 B2 | 5/2010 | Biedermann et al. |
| 7,727,261 B2 | 6/2010 | Barker |
| 7,731,736 B2 | 6/2010 | Guenther et al. |
| 7,736,380 B2 | 6/2010 | Johnston et al. |
| 7,766,946 B2 | 8/2010 | Bailly |
| 7,785,354 B2 | 8/2010 | Biedermann et al. |
| 7,789,900 B2 | 9/2010 | Levy et al. |
| 7,846,190 B2 | 12/2010 | Ball |
| 7,850,718 B2 | 12/2010 | Bette et al. |
| 7,857,834 B2 | 12/2010 | Boschert |
| 7,867,257 B2 | 1/2011 | Na et al. |
| 7,892,259 B2 | 2/2011 | Biedermann et al. |
| 7,901,413 B1 | 3/2011 | Lewis |
| 7,922,748 B2 | 4/2011 | Hoffman |
| 7,951,173 B2 | 5/2011 | Hammill, Sr. et al. |
| 7,951,175 B2 | 5/2011 | Chao et al. |
| 7,955,363 B2 | 6/2011 | Richelsoph |
| 8,007,522 B2 | 8/2011 | Hutchinson |
| 8,016,862 B2 | 9/2011 | Felix et al. |
| 8,052,724 B2 | 11/2011 | Jackson |
| 8,057,518 B2 | 11/2011 | Frasier et al. |
| 8,066,744 B2 | 11/2011 | Justis et al. |
| 8,066,745 B2 | 11/2011 | Kirschman |
| 8,075,599 B2 | 12/2011 | Johnson et al. |
| 8,083,774 B2 | 12/2011 | Teitelbaum |
| 8,092,494 B2 | 1/2012 | Butler et al. |
| 8,097,023 B2 | 1/2012 | Cline, Jr. et al. |
| 8,097,025 B2 | 1/2012 | Hawkes et al. |
| 8,100,946 B2 | 1/2012 | Strausbaugh et al. |
| 8,114,134 B2 | 2/2012 | Winslow et al. |
| 8,162,989 B2 | 4/2012 | Khalili |
| 8,167,910 B2 | 5/2012 | Nilsson |
| 8,167,912 B2 | 5/2012 | Jacofsky et al. |
| 8,197,517 B1 | 6/2012 | Lab et al. |
| 8,197,518 B2 | 6/2012 | Hammill, Sr. et al. |
| 8,221,471 B2 | 7/2012 | Kovach et al. |
| 8,221,472 B2 | 7/2012 | Peterson et al. |
| 8,236,035 B1 | 8/2012 | Bedor |
| 8,241,341 B2 | 8/2012 | Walker et al. |
| 8,257,396 B2 | 9/2012 | Jackson |
| 8,257,399 B2 | 9/2012 | Biedermann et al. |
| 8,267,968 B2 | 9/2012 | Remington et al. |
| 8,273,112 B2 | 9/2012 | Garamszegi et al. |
| 8,277,490 B2 | 10/2012 | Freeman et al. |
| 8,287,576 B2 | 10/2012 | Barrus |
| 8,298,270 B2 | 10/2012 | Justis et al. |
| 8,298,274 B2 | 10/2012 | Barker, Jr. et al. |
| 8,303,594 B2 | 11/2012 | Lynch et al. |
| 8,308,782 B2 | 11/2012 | Jackson |
| 8,313,515 B2 | 11/2012 | Brennan et al. |
| 8,313,516 B2 | 11/2012 | Konieczynski et al. |

(56) References Cited

U.S. PATENT DOCUMENTS

| | | |
|---|---|---|
| 8,337,530 B2 | 12/2012 | Hestad et al. |
| 8,343,191 B2 | 1/2013 | Matthis et al. |
| 8,377,100 B2 | 2/2013 | Jackson |
| 8,409,260 B2 | 4/2013 | Biedermann et al. |
| 8,430,914 B2 | 4/2013 | Spratt et al. |
| 8,465,528 B2 | 6/2013 | Schumacher |
| 8,465,530 B2 | 6/2013 | Hammill, Sr. et al. |
| 8,491,640 B1 | 7/2013 | Robinson |
| 8,491,641 B2 | 7/2013 | Nihalani |
| 8,556,938 B2 | 10/2013 | Jackson et al. |
| 8,556,941 B2 | 10/2013 | Hutchinson |
| 8,608,746 B2 | 12/2013 | Kolb et al. |
| 8,951,294 B2 | 2/2015 | Gennari et al. |
| 9,155,580 B2 | 10/2015 | Cormier et al. |
| 9,259,247 B2 | 2/2016 | Chandanson et al. |
| 9,402,673 B2 | 8/2016 | Cormier et al. |
| 9,433,445 B2 | 9/2016 | Ramsay et al. |
| 9,662,143 B2 | 5/2017 | Jackson |
| RE46,431 E | 6/2017 | Jackson |
| 9,700,354 B2 | 7/2017 | Jackson |
| 9,713,488 B2 | 7/2017 | Hutchinson |
| 9,724,130 B2 | 8/2017 | Chandanson et al. |
| 9,724,145 B2 | 8/2017 | Spratt et al. |
| 9,775,660 B2 | 10/2017 | Spratt et al. |
| 9,782,204 B2 | 10/2017 | Spratt et al. |
| 9,788,866 B2 | 10/2017 | Jackson |
| 9,801,665 B2 | 10/2017 | Jackson |
| 9,918,747 B2 | 3/2018 | Spratt et al. |
| 2002/0058942 A1 | 5/2002 | Biedermann et al. |
| 2002/0133159 A1 | 9/2002 | Jackson |
| 2003/0023243 A1 | 1/2003 | Biedermann et al. |
| 2003/0055426 A1 | 3/2003 | Carbone et al. |
| 2003/0073996 A1 | 4/2003 | Doubler et al. |
| 2003/0100896 A1 | 5/2003 | Biedermann et al. |
| 2003/0125741 A1 | 7/2003 | Biedermann et al. |
| 2003/0153911 A1 | 8/2003 | Shluzas |
| 2004/0049190 A1 | 3/2004 | Biedermann et al. |
| 2004/0116929 A1 | 6/2004 | Barker et al. |
| 2004/0153077 A1 | 8/2004 | Biedermann et al. |
| 2004/0162560 A1 | 8/2004 | Raynor et al. |
| 2004/0186473 A1 | 9/2004 | Cournoyer et al. |
| 2004/0186478 A1 | 9/2004 | Jackson |
| 2004/0193160 A1 | 9/2004 | Richelsoph |
| 2004/0243126 A1 | 12/2004 | Carbone et al. |
| 2005/0055026 A1 | 3/2005 | Biedermann et al. |
| 2005/0080415 A1 | 4/2005 | Keyer et al. |
| 2005/0153077 A1 | 7/2005 | Gedeon et al. |
| 2005/0154391 A1 | 7/2005 | Doherty et al. |
| 2005/0154393 A1 | 7/2005 | Doherty et al. |
| 2005/0159750 A1 | 7/2005 | Doherty |
| 2005/0182401 A1 | 8/2005 | Timm et al. |
| 2005/0187548 A1 | 8/2005 | Butler et al. |
| 2005/0216003 A1 | 9/2005 | Biedermann et al. |
| 2005/0228326 A1 | 10/2005 | Kalfas et al. |
| 2005/0273101 A1 | 12/2005 | Schumacher |
| 2005/0277928 A1 | 12/2005 | Boschert |
| 2006/0025771 A1 | 2/2006 | Jackson |
| 2006/0083603 A1 | 4/2006 | Jackson |
| 2006/0084995 A1 | 4/2006 | Biedermann et al. |
| 2006/0100621 A1 | 5/2006 | Jackson |
| 2006/0100622 A1 | 5/2006 | Jackson |
| 2006/0106383 A1 | 5/2006 | Biedermann et al. |
| 2006/0149241 A1 | 7/2006 | Richelsoph et al. |
| 2006/0161153 A1 | 7/2006 | Hawkes et al. |
| 2006/0200128 A1 | 9/2006 | Mueller |
| 2006/0241599 A1 | 10/2006 | Konieczynski et al. |
| 2006/0264933 A1 | 11/2006 | Baker et al. |
| 2007/0055244 A1 | 3/2007 | Jackson |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0123870 A1 | 5/2007 | Jeon et al. |
| 2007/0233078 A1* | 10/2007 | Justis ................ A61B 17/7035 606/279 |
| 2007/0260246 A1 | 11/2007 | Biedermann |
| 2007/0265621 A1 | 11/2007 | Matthis et al. |
| 2007/0270813 A1 | 11/2007 | Garamszegi |
| 2007/0293862 A1 | 12/2007 | Jackson |
| 2008/0021473 A1 | 1/2008 | Butler et al. |
| 2008/0045953 A1 | 2/2008 | Garamszegi |
| 2008/0119852 A1 | 5/2008 | Dalton et al. |
| 2008/0132957 A1 | 6/2008 | Matthis et al. |
| 2008/0147129 A1 | 6/2008 | Biedermann et al. |
| 2008/0161859 A1 | 7/2008 | Nilsson |
| 2008/0200956 A1 | 8/2008 | Beckwith et al. |
| 2008/0215100 A1 | 9/2008 | Matthis et al. |
| 2008/0269805 A1 | 10/2008 | Dekutoski et al. |
| 2008/0269809 A1 | 10/2008 | Garamszegi |
| 2008/0288001 A1 | 11/2008 | Cawley et al. |
| 2008/0294202 A1 | 11/2008 | Peterson et al. |
| 2008/0312692 A1 | 12/2008 | Brennan et al. |
| 2009/0005813 A1 | 1/2009 | Crall et al. |
| 2009/0012567 A1 | 1/2009 | Biedermann et al. |
| 2009/0018591 A1 | 1/2009 | Hawkes et al. |
| 2009/0062861 A1 | 3/2009 | Frasier et al. |
| 2009/0118772 A1 | 5/2009 | Diederich et al. |
| 2009/0163962 A1 | 6/2009 | Dauster et al. |
| 2009/0182384 A1 | 7/2009 | Wilcox et al. |
| 2009/0198280 A1 | 8/2009 | Spratt et al. |
| 2009/0216280 A1 | 8/2009 | Hutchinson |
| 2009/0228051 A1 | 9/2009 | Kolb et al. |
| 2009/0228053 A1 | 9/2009 | Kolb et al. |
| 2009/0254125 A1 | 10/2009 | Predick |
| 2009/0264896 A1* | 10/2009 | Biedermann ...... A61B 17/7037 606/104 |
| 2009/0264933 A1 | 10/2009 | Carls et al. |
| 2009/0287261 A1 | 11/2009 | Jackson |
| 2009/0326587 A1 | 12/2009 | Matthis et al. |
| 2010/0004693 A1 | 1/2010 | Miller et al. |
| 2010/0010547 A1 | 1/2010 | Beaurain et al. |
| 2010/0020272 A1 | 1/2010 | Kim et al. |
| 2010/0023061 A1 | 1/2010 | Randol et al. |
| 2010/0030272 A1 | 2/2010 | Winslow et al. |
| 2010/0103099 A1 | 4/2010 | Lee |
| 2010/0114174 A1 | 5/2010 | Jones et al. |
| 2010/0152785 A1 | 6/2010 | Forton et al. |
| 2010/0160977 A1 | 6/2010 | Gephart et al. |
| 2010/0168747 A1 | 7/2010 | Lynch et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222827 A1 | 9/2010 | Griffiths et al. |
| 2010/0234891 A1 | 9/2010 | Freeman et al. |
| 2010/0305621 A1 | 12/2010 | Wang et al. |
| 2010/0312279 A1* | 12/2010 | Gephart ............. A61B 17/3421 606/264 |
| 2011/0046683 A1 | 2/2011 | Biedermann et al. |
| 2011/0106179 A1 | 5/2011 | Prevost et al. |
| 2011/0160778 A1 | 6/2011 | Elsbury |
| 2011/0160779 A1 | 6/2011 | Schlaepfer et al. |
| 2011/0190822 A1 | 8/2011 | Spitler et al. |
| 2011/0213424 A1 | 9/2011 | Biedermann et al. |
| 2011/0245876 A1 | 10/2011 | Brumfield |
| 2011/0245877 A1 | 10/2011 | Pisharodi |
| 2011/0251650 A1 | 10/2011 | Biedermann et al. |
| 2011/0270322 A1 | 11/2011 | Olsen et al. |
| 2011/0276098 A1 | 11/2011 | Biedermann et al. |
| 2011/0282399 A1 | 11/2011 | Jackson |
| 2011/0288592 A1 | 11/2011 | McKinley |
| 2011/0288599 A1 | 11/2011 | Michielli et al. |
| 2011/0295321 A1 | 12/2011 | Hutchinson |
| 2012/0010661 A1 | 1/2012 | Farris et al. |
| 2012/0022593 A1 | 1/2012 | Kovach et al. |
| 2012/0035670 A1 | 2/2012 | Jackson et al. |
| 2012/0046701 A1 | 2/2012 | Gennari et al. |
| 2012/0059425 A1 | 3/2012 | Biedermann |
| 2012/0059426 A1 | 3/2012 | Jackson et al. |
| 2012/0078307 A1 | 3/2012 | Nihalani |
| 2012/0083845 A1 | 4/2012 | Winslow et al. |
| 2012/0089194 A1 | 4/2012 | Strausbaugh et al. |
| 2012/0136395 A1 | 5/2012 | Biedermann et al. |
| 2012/0143266 A1 | 6/2012 | Jackson et al. |
| 2012/0150239 A1 | 6/2012 | Garamszegi |

(56) References Cited

U.S. PATENT DOCUMENTS

| | | | |
|---|---|---|---|
| 2012/0165881 A1* | 6/2012 | Biedermann | A61B 17/7037 606/328 |
| 2012/0165882 A1 | 6/2012 | Biedermann et al. | |
| 2012/0179209 A1 | 7/2012 | Biedermann et al. | |
| 2012/0185003 A1 | 7/2012 | Biedermann et al. | |
| 2012/0197313 A1 | 8/2012 | Cowan | |
| 2012/0209336 A1 | 8/2012 | Jackson et al. | |
| 2012/0253404 A1 | 10/2012 | Timm et al. | |
| 2012/0277805 A1 | 11/2012 | Farris | |
| 2012/0303070 A1 | 11/2012 | Jackson | |
| 2012/0310290 A1 | 12/2012 | Jackson | |
| 2012/0316605 A1 | 12/2012 | Palagi | |
| 2012/0328394 A1 | 12/2012 | Biedermann et al. | |
| 2012/0330364 A1 | 12/2012 | Jacofsky et al. | |
| 2013/0013003 A1 | 1/2013 | Carbone et al. | |
| 2013/0046350 A1 | 2/2013 | Jackson et al. | |
| 2013/0053901 A1 | 2/2013 | Cormier et al. | |
| 2013/0096618 A1 | 4/2013 | Chandanson et al. | |
| 2013/0096623 A1 | 4/2013 | Biedermann et al. | |
| 2013/0103093 A1 | 4/2013 | Biedermann et al. | |
| 2013/0110172 A1 | 5/2013 | Biedermann et al. | |
| 2013/0110180 A1 | 5/2013 | Doubler et al. | |
| 2013/0144346 A1* | 6/2013 | Jackson | A61B 17/8605 606/305 |
| 2013/0211467 A1* | 8/2013 | Dickinson | A61B 17/7034 606/328 |
| 2014/0018861 A1 | 1/2014 | Hutchinson | |
| 2014/0025119 A1 | 1/2014 | Biedermann et al. | |
| 2014/0094849 A1 | 4/2014 | Spratt et al. | |
| 2014/0142633 A1 | 5/2014 | Jackson et al. | |
| 2014/0142634 A1 | 5/2014 | Schlaepfer et al. | |
| 2014/0277153 A1 | 9/2014 | Spratt et al. | |
| 2014/0277157 A1 | 9/2014 | Chandanson et al. | |
| 2014/0277158 A1 | 9/2014 | Spratt et al. | |
| 2014/0277159 A1 | 9/2014 | Spratt et al. | |
| 2014/0277161 A1 | 9/2014 | Spratt et al. | |
| 2014/0277162 A1 | 9/2014 | Kostuik et al. | |
| 2014/0277189 A1 | 9/2014 | Spratt et al. | |
| 2015/0173816 A1* | 6/2015 | Biedermann | A61B 17/8605 606/308 |
| 2016/0128733 A1 | 5/2016 | Spratt et al. | |
| 2016/0135848 A1 | 5/2016 | Chandanson et al. | |
| 2017/0296235 A1 | 10/2017 | Chandanson et al. | |
| 2017/0354446 A1 | 12/2017 | Spratt et al. | |
| 2017/0354448 A1 | 12/2017 | Hutchinson | |
| 2017/0360482 A1 | 12/2017 | Spratt et al. | |

FOREIGN PATENT DOCUMENTS

| | | |
|---|---|---|
| EP | 0 857 465 A1 | 8/1998 |
| EP | 1 295 566 A1 | 3/2003 |
| EP | 1 570 794 A1 | 9/2005 |
| EP | 1 694 229 A1 | 8/2006 |
| EP | 1 774 919 A1 | 4/2007 |
| EP | 1 795 134 A1 | 6/2007 |
| EP | 2 070 485 A1 | 6/2009 |
| EP | 2 129 310 A1 | 12/2009 |
| EP | 2 272 451 A1 | 1/2011 |
| EP | 2 286 748 A1 | 2/2011 |
| EP | 2 455 028 A1 | 5/2012 |
| WO | 91/16020 A1 | 10/1991 |
| WO | 2004/058081 A1 | 7/2004 |
| WO | 2008/024937 A2 | 2/2008 |
| WO | 2008/119006 A1 | 10/2008 |
| WO | 2009/073655 A1 | 6/2009 |
| WO | 2010/056846 A2 | 5/2010 |
| WO | 2011/059732 A1 | 5/2011 |
| WO | 2011/109009 A1 | 9/2011 |
| WO | 2011/127065 A1 | 10/2011 |
| WO | 2012/024665 A2 | 2/2012 |
| WO | 2012/030712 A1 | 3/2012 |
| WO | 2012/035479 A2 | 3/2012 |
| WO | 2012/060868 A1 | 5/2012 |
| WO | 2013/028851 A1 | 2/2013 |

OTHER PUBLICATIONS

[No Author Listed] Definition of "clip," www.thefreedictionary.com/clip; accessed May 16, 2015.

[No Author Listed] Expedium Spine System, Dual Innie Independent Locking Technology Brochure, DePuy Spine, Aug. 1, 2004, 6 pages.

[No Author Listed] Moss Miami Polyaxial Reduction Screw Surgical Technique, DePuy AcroMed, Inc. 1998.

[No Author Listed] Straight Talk with Expedium. Expedium. 10 pages. Jul. 2007.

[No Author Listed] Surgical Technique Guide and Ordering Information. Expedium. DePuy Spine Inc. Sep. 2011. 24 pages.

[No Author Listed] Value Analysis Brief—Expedium Favored Angle Screw. DePuy Synthes Spine. Aug. 2012. 4 pages.

[No Author Listed] Viper 2 MIS Extended Tab , DePuy Spine, Inc., Feb. 1, 2009.

[No Author Listed] Viper 2 MIS Spine System. System Guide. DePuy Spine Inc. Sep. 2011. 60 pages.

Duerig, T. W., et al., "An Engineer's Perspective of Pseudoelasticity," p. 370, in Engineering Aspects of Shape Memory Alloys, Butterworth-Heinemann, 1990.

International Search Report and Written Opinion for Application No. PCT/US2013/060350, dated Jan. 3, 2014 (9 pages).

International Search Report for PCT/US14/021198 dated Jun. 5, 2014 (3 pages).

International Preliminary Report on Patentability for Application No. PCT/US2014/021198, dated Sep. 24, 2015 (7 pages).

U.S. Appl. No. 61/706,860, filed Sep. 28, 2012 (66 pages).

U.S. Appl. No. 12/365,225, filed Feb. 4, 2009, Methods for Correction of Spinal Deformities.

U.S. Appl. No. 13/205,248, filed Aug. 8, 2011, Methods for Correction of Spinal Deformities.

U.S. Appl. No. 13/804,012, filed Mar. 14, 2013, Bone Anchors and Surgical Instruments With Integrated Guide Tips.

U.S. Appl. No. 13/826,161, filed Mar. 14, 2013, Bone Anchor Assemblies and Methods With Improved Locking.

U.S. Appl. No. 13/827,092, filed Mar. 14, 2013, Locking Compression Members for Use With Bone Anchor Assemblies and Methods.

U.S. Appl. No. 13/828,236, filed Mar. 14, 2013, Bone Anchor Assemblies With Multiple Component Bottom Loading Bone Anchors.

U.S. Appl. No. 13/828,882, filed Mar. 14, 2013, Bottom-Loading Bone Anchor Assemblies and Methods.

U.S. Appl. No. 13/829,000, filed Mar. 14, 2013, Bottom-Loading Bone Anchor Assemblies.

U.S. Appl. No. 14/029,005, filed Sep. 17, 2013, Bone Anchor Assemblies.

U.S. Appl. No. 14/029,037, filed Sep. 17, 2013, Methods for Correction of Spinal Deformities.

U.S. Appl. No. 14/070,943, filed Nov. 4, 2013, Bone Anchor Assemblies and Methods With Improved Locking.

U.S. Appl. No. 14/966,531, filed Dec. 11, 2015, Bone Anchor Assemblies and Methods With Improved Locking.

U.S. Appl. No. 14/987,812, filed Jan. 5, 2016, Locking Compression Members for Use With Bone Anchor Assemblies and Methods.

U.S. Appl. No. 15/629,825, filed Jun. 22, 2017, Methods for Correction of Spinal Deformities.

U.S. Appl. No. 15/634,630, filed Jun. 27, 2017, Bone Anchor Assemblies With Multiple Component Bottom Loading Bone Anchors.

U.S. Appl. No. 15/643,075, filed Jul. 6, 2017, Locking Compression Members for Use With Bone Anchor Assemblies and Methods.

U.S. Appl. No. 15/692,166, filed Aug. 31, 2017, Bone Anchor Assemblies.

U.S. Appl. No. 61/706,860, filed Sep. 28, 2012, Devices and Methods for Breaking and Retaining Surgical Reduction Tabs.

U.S. Appl. No. 61/707,062, filed Sep. 28, 2012, Bone Anchor Assemblies.

\* cited by examiner

BOTTOM-LOADING BONE ANCHOR ASSEMBLIES AND METHODS

CROSS REFERENCE TO RELATED APPLICATIONS

This application is a continuation of U.S. application Ser. No. 13/828,882, filed on Mar. 14, 2013, now issued as U.S. Pat. No. 9,775,660, which is hereby incorporated by reference in its entirety.

FIELD

The present invention relates to methods and devices for correcting a spine, and in particular to bone anchor assemblies and method s of using the same.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a bone anchor with a threaded shank that is adapted to be threaded into a vertebra, and a rod-receiving element, usually in the form of a head having opposed U-shaped slots formed therein. The shank and rod-receiving assembly can be provided as a monoaxial assembly, whereby the rod-receiving element is fixed with respect to the shank, a unidirectional assembly, wherein the shank is limited to movement in a particular direction, e.g., within a single plane, or a polyaxial assembly, whereby the rod-receiving element has free angular movement with respect to the shank. In use, the shank portion of each screw is threaded into a vertebra, and once properly positioned, a fixation rod is seated into the rod-receiving element of each screw. The rod is then locked in place by tightening a set-screw, plug, or similar type of fastening mechanism onto the rod-receiving element.

In certain procedures, it is desirable to utilize a bone anchor, such as a bone screw, having a large diameter shank. Large diameter shanks typically require larger heads on the bone screw, which undesirably increases the bone anchor assembly profile. Such large diameter bone screws often utilize a bottom-loading configuration, in which the head of the threaded shank is loaded into an opening in the bottom of the rod-receiving element. This can be done during manufacturing, or intraoperatively either before or after the threaded shank is implanted in bone. This allows the diameter of the shank to remain independent of the size of the opening formed in the rod-receiving element. However, angulation and the ability to perform correctional techniques with such bottom-loading bone anchor assemblies can be limited. Such bone anchor assemblies can break or separate as a result of extreme angulation. This problem is exacerbated with favored-angle bone anchor assemblies, in which a bottom surface of the receiver member is angled such that a cone of angulation of the bone anchor relative to the receiver member is biased in one direction. These devices must be able to withstand tensional forces applied thereto when the rod-receiving element is angulated relative to the shank or during bending of a spinal fixation rod seated therein.

Accordingly, there remains a need for improved devices and methods for correcting a spine, and in particular to improved bottom-loading anchor assemblies and methods.

SUMMARY

Various bone anchor assemblies and methods are provided having a multi-component bone anchor that is configured to allow bottom-loading of the bone anchor into a receiver member during use, and to provide secure fixation between the receiver member and the bone anchor. Such a configuration can be particularly useful with favored-angle bone anchors in which the bottom surface of the receiver member is angled such that the cone of angulation of the bone anchor relative to the receiver member is biased in one direction.

In one embodiment, a bone anchor assembly is provided and includes a shank having a distal threaded portion and a proximal head portion, a ball having a spherical exterior surface and a central lumen sized to receive the head portion of the shank, and a clip configured to be engaged between the head portion and the ball such that the clip is effective to lock the ball in engagement with the shank. In one embodiment, the central lumen of the ball can be cylindrical and the head of the shank can be cylindrical to fit within the central lumen. The clip can engage the head and the ball using various techniques. For example, the head portion can have a first annular groove formed therein and the central lumen can include a second annular groove formed therein, and the clip can be configured to extend into the first annular groove and the second annular groove when the clip is engaged between the head portion and the ball. The bone anchor assembly can also include a receiver member having an aperture formed in a distal end thereof and sized such that the head portion of the shank can pass through the aperture and such that the ball cannot pass through the aperture. In an exemplary embodiment, a major diameter of the distal threaded portion of the shank is greater than a diameter of the aperture formed in the receiver member.

In certain embodiments, a height of the first groove and a height of the second groove are substantially the same as a height of the clip such that, when mated, the ball and the shank are locked in a fixed axial position relative to one another. In an exemplary embodiment, at least one of the first and second grooves has a depth that is equal to or greater than a width of the clip. The clip can be, for example, a circlip. In another embodiment, the clip can be a C-shaped band having a radial cut formed therein, a first side of the radial cut having a tab configured to interlock with a complementary recess formed in a second side of the radial cut. In another embodiment, the clip can be a continuous ring formed from an expandable material, such as a shape memory alloy.

In other embodiments, the head portion of the shank can taper towards its proximal end to provide a lead-in surface for expanding the clip as the clip is slid distally over the head portion and into the first groove during assembly. In certain aspects, a proximal end of the head portion is defined by a spherical surface having a common center point with the spherical exterior surface of the ball when the ball is mated to the shank. The head portion can include a driving interface formed therein for driving the shank into bone. In one embodiment, the first annular groove can intersect with the driving interface and the clip can be configured to bear against instruments inserted into the driving interface to retain the shank on such instruments.

Methods of assembling a bone anchor assembly are also provided and in one embodiment the method includes engaging a clip with one of a first annular groove formed in a proximal head portion of a shank and a second annular groove formed in a central lumen of a ball having a spherical exterior surface, positioning the ball in a seat portion of a receiver member, and advancing the head portion of the shank proximally through an aperture formed in a distal end of the receiver member and into the central lumen of the ball until the clip engages the other of the first annular groove and the second annular groove to lock the ball in engagement with the shank and to thereby secure the shank to the receiver member. The method can also include implanting a threaded distal portion of the shank in bone and polyaxially moving the receiver member relative to the shank, and positioning a spinal fixation element within the receiver member and applying a closure mechanism to the receiver member to lock the receiver member in a fixed position relative to the shank. In one embodiment, the clip is expanded over a tapered lead formed at a proximal end of the head portion.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1A:
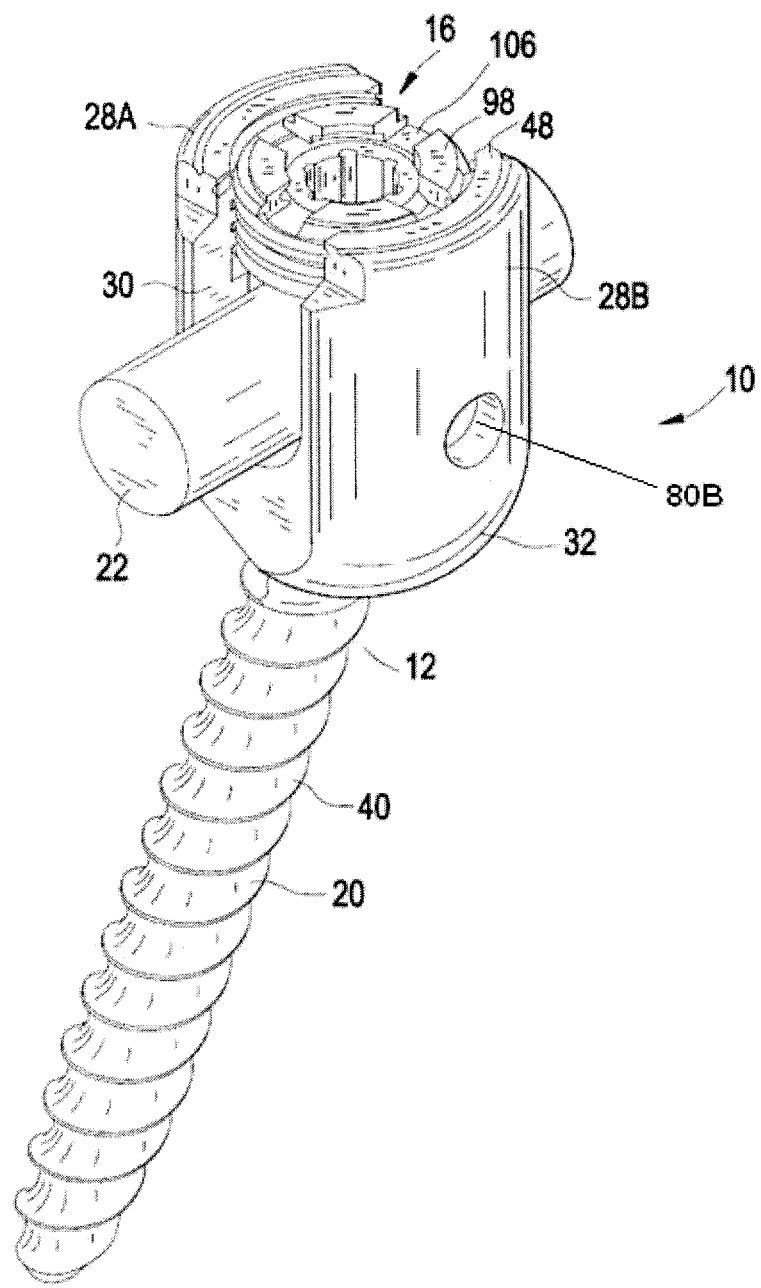
FIG. 1A is a perspective view of a prior art bone anchor assembly.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, various bone anchor assemblies and methods are provided having a multi-component bone anchor that is configured to allow the shank of the bone anchor to be bottom-loaded into a receiver member before or during a procedure. Such devices and methods can allow for the use of bone anchors having large diameter shanks capable of withstanding greater bending forces, while still utilizing a relatively low-profile receiver member for coupling a spinal fixation element to the bone anchor. The bone anchor assemblies and methods can also be particularly useful with favored-angle bone anchors in which a cone of angulation of the bone anchor relative to the receiver member is biased in one direction.

FIGS. 1A-1D illustrate a prior art bone anchor assembly 10 including a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone screw designed for posterior implantation in the pedicle or lateral mass of a vertebra. The proximal head 18 of the bone anchor 12 engages the distal end 32 of the receiver member 14 in a ball and socket like arrangement in which the proximal head 18 the distal shaft 20 can pivot relative to the receiver member 14, i.e., the distal end 32 defines a polyaxial seat on a proximal surface thereof for the bone anchor 12. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Provisional Patent Application Ser. No. 61/527,389, filed Aug. 25, 2011, both of which are incorporated herein by reference. The distal shaft 20 can also include other structures for engaging bone, including a hook. The distal shaft 20 of the bone anchor 12 can be cannulated, having a central passage or cannula extending the length of the bone anchor to facilitate delivery of the bone anchor over a guide wire in, for example, minimally-invasive procedures. Other components of the bone anchor assembly, including, for example, the closure member 16, the receiver member 14, and the compression member 60 (discussed below) can be cannulated or otherwise have an opening to permit delivery over a guide wire. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated herein by reference. The distal shaft 20 of the bone anchor 12 can also be coated with materials to permit bone growth, such as, for example, hydroxyapatite, and the bone anchor assembly 10 can be coated partially or entirely with anti-infective materials, such as, for example, tryclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated herein by reference. At least a portion of the proximal end surface 48 of the receiver member 12 defines a plane Y. The receiver member 14 has a central longitudinal axis L.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening. At least a portion of the distal end surface 34 defines a plane X.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The illustrated bone anchor is a favored-angle polyaxial screw in which the cone of angulation is biased in one direction. In this manner, the bone anchor 12 is movable relative to the receiver member 14 in at least a first direction, indicated by arrow A in FIG. 1D, at a first angle C relative to the central longitudinal axis L of the receiver member 14. The bone anchor 12 is also movable in at least a second direction, indicated by arrow B in FIG. 1D, at a second angle D relative to the longitudinal axis L. The first angle C is greater than the second angle D and, thus, the shaft 20 of the bone anchor 12 is movable more in the direction indicated by arrow A than in the direction indicated by arrow B. The distal shaft 20 of the bone anchor 12 defines a neutral axis 48 with respect to the receiver member 14. The neutral axis 48 can be perpendicular to the plane X defined by the distal end surface 34 and intersects the center point of the opening in the distal end surface 34 through which the distal shaft 20 of the bone anchor 12 extends. The neutral axis 48 can be oriented at an angle to the central longitudinal axis L of the receiver member 14. The plane Y defined by at least a portion of the proximal end surface 48 of the receiver member 14 intersects the plane X defined by at least a portion of the distal end surface 34 of the receiver member 12. The proximal end 26 of the receiver member 14 can include a proximal first bore 50 coaxial with a first central longitudinal axis N (which is coincident with longitudinal axis L) and a distal second bore 52 coaxial with a second central longitudinal axis M (which is coincident with the neutral axis 48) and the first central longitudinal axis N and second central longitudinal axis M can intersect one another. The angle between the plane X and the plane Y and the angle between the axis L and the axis M can be selected to provide the desired degree of biased angulation. Examples of favored angled polyaxial screws are described in more detail in U.S. Pat. No. 6,974,460, issued on Dec. 13, 2005, and in U.S. Pat. No. 6,736,820, issued on May 18, 2004, both of which are hereby incorporated herein by reference. Alternatively, the bone anchor assembly can be a conventional (non-biased) polyaxial screw in which the bone anchor pivots in the same amount in every direction and has a neutral axis that is coincident with the central longitudinal axis L of the receiver member.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. The compression member 60 can include a pair of spaced apart arms 62A and 62B defining a U-shaped seat 64 for receiving the spinal rod 22 and a distal surface 66 for engaging the proximal head 18 of the bone anchor 12.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In the illustrated embodiment, however, the closure mechanism 16 comprises an outer set screw 70 positionable between and engaging the arms 28A, 28B of the receiver member 14 and an inner set screw 72 positionable within the outer set screw 70. The outer set screw 70 is operable to act on the compression member 60 to fix the bone anchor 12 relative to the receiver member 14. The inner set screw 72 is operable to act on the spinal rod 22 to fix the spinal rod 22 relative to the receiver member 14. In this manner, the closure mechanism 16 permits the bone anchor 12 to be fixed relative to the receiver member 14 independently of the spinal rod 22 being fixed to the receiver member 14. In particular, the outer set screw 70 can engage the proximal end surfaces of the arms 62A, 62B of the compression member 60 to force the distal surface 66 of the compression member 60 into contact with the proximal head 18 of bone anchor 12, which in turn forces the distal surface 38 of the proximal head 18 into fixed engagement with the distal inner surface of the receiver member 14. The inner set screw 72 can engage the spinal rod 22 to force the spinal rod 22 into fixed engagement with the rod seat 64 of the compression member 60.

The outer set screw 70 includes a first outer thread 74 for engaging a complementary inner thread 42 on the arms 28A, 28B of the receiver member 14. The outer set screw 74 includes a central passage 96 from a top surface 98 of the outer set screw 74 to a bottom surface 100 of the outer set screw 74 for receiving the inner set screw 72. The central passage 96 can includes an inner thread 102 for engaging a complementary outer thread 104 on the inner set screw 72. The thread form for the inner thread 102 and the outer thread 104, including the number of threads, the pitch, major and minor diameter, and thread shape, can be selected to facilitate connection between the components and transfer of the desired axial tightening force. The top surface 98 of the outer set screw 74 can have one or more drive features to facilitate rotation and advancement of the outer set screw 74 relative to the receiver member 14. The illustrated outer set screw 74 includes drive features in the form of a plurality of cut-outs 106 spaced-apart about the perimeter of the top surface 98. The inner set screw 104 can include drive features for receiving an instrument to rotate and advance the inner set screw 72 relative to the outer set screw 74. The illustrated inner set screw 104 includes drive features in the form of a central passage 108 having a plurality of spaced apart, longitudinally oriented cut-outs for engaging complementary features on an instrument.

The bone anchor assembly 10 can be used with a spinal fixation element such as rigid spinal rod 22. The various components of the bone anchor assemblies disclosed herein, as well as the spinal rod 22, can be constructed from various materials, including titanium, titanium alloys, stainless steel, cobalt chrome, PEEK, or other materials suitable for rigid fixation. In other embodiments, the spinal fixation element can be a dynamic stabilization member that allows controlled mobility between the instrumented vertebrae.

In use, bone can be prepared to receive the bone anchor assembly 10, generally by drilling a hole in the bone which is sized appropriately to receive the bone anchor 12. If not already completed, the bone anchor assembly 10 can be assembled, which can include assembling the bone anchor 12 and the receiver member 14, so that the distal shaft 20 extends through the opening in the distal end 32 of the receiver member 14 and the proximal head 18 of the bone anchor 12 is received in the distal end 32 of the receiver member 14. A driver tool can be fitted with the bone anchor 12 to drive the bone anchor 12 into the prepared hole in the bone. The compression member 60 can be positioned within the receiver member 14 such that the arms 62A, 62B of the compression member are aligned with the arms 28A, 28B of the receiver member 14 and the lower surface of the compression member 14 is in contact with the proximal head 18 of the bone anchor 12. A spinal fixation element, e.g., the spinal rod 22, can be located in the recess 30 of the receiver member 14. The closure mechanism 16 can be engaged with the inner thread 42 provided on the arms 28A, 28B of the receiver member 14. A torsional force can be applied to the outer set screw 70 to move it within the recess 30 using a tool which can engage the plurality of cut-outs 106 in the upper facing surface of the outer set screw 70, so as to force the compression member 60 onto the proximal head 18 of the bone anchor 12. Torsional forces can then be applied to the inner set screw 72 to move it relative to the outer set screw 70 so that it contacts the spinal rod 22 and can, for example, fix the spinal rod 22 relative to the receiver member 14 and the bone anchor 12.

One or more embodiments of inventive bone anchor assemblies are described below. Except as indicated below, the structure, operation, and use of these embodiments is similar or identical to that of the bone anchor assembly 10 described above. Accordingly, a detailed description of said structure, operation, and use is omitted here for the sake of brevity.

Figure 1B:
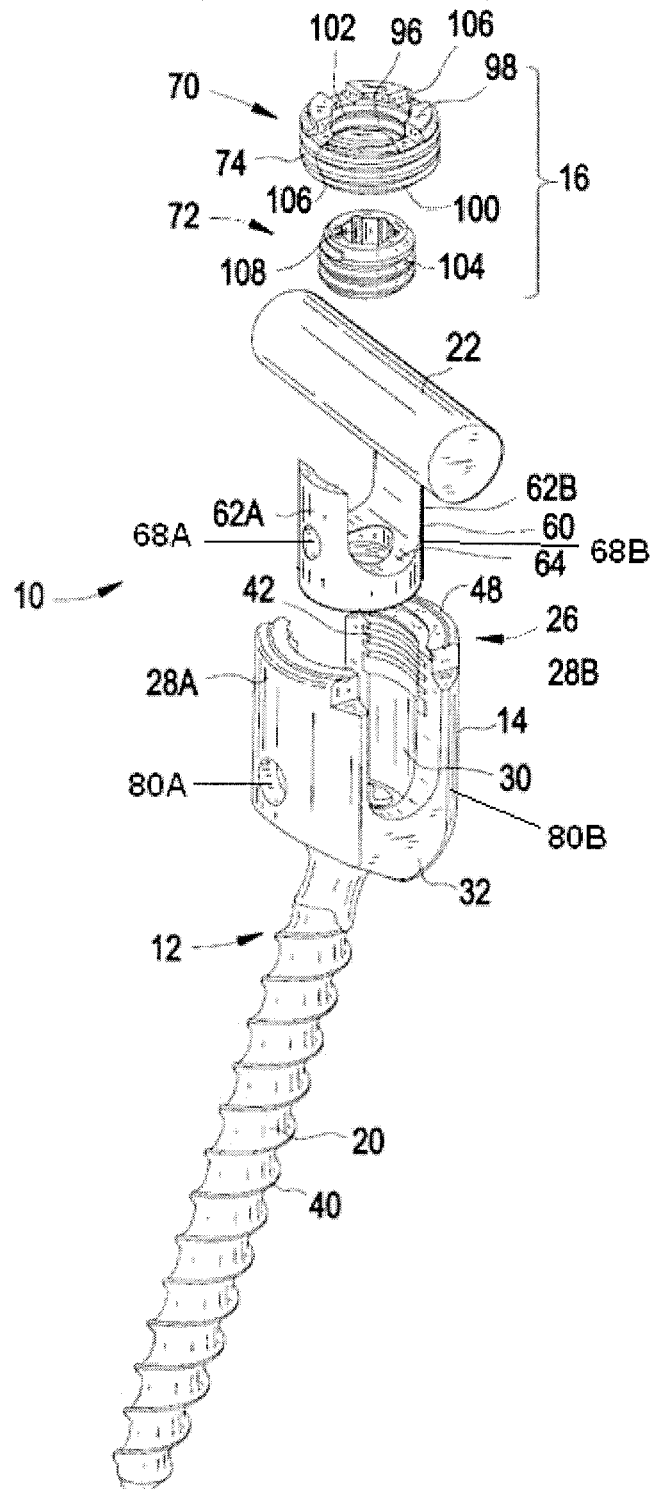
FIG. 1B is an exploded view of the bone anchor assembly of FIG. 1A.
Figure 1C:
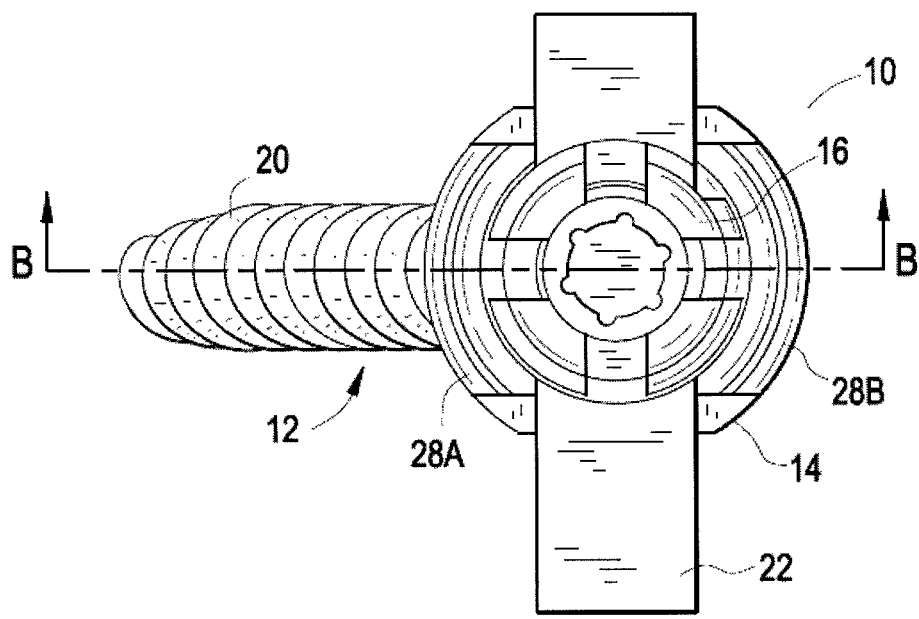
FIG. 1C is a top view of the bone anchor assembly of FIG. 1A.
Figure 1D:
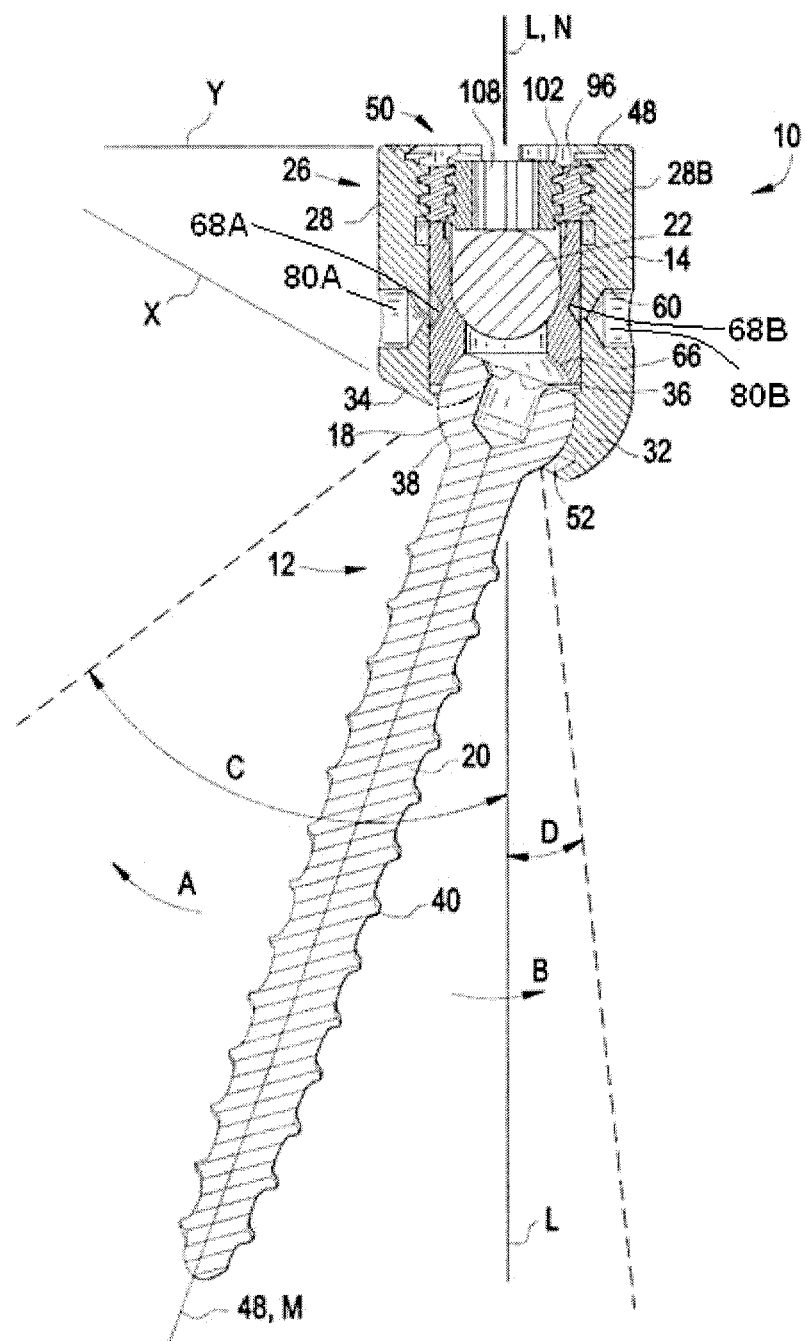
FIG. 1D is a cross-sectional view of the bone anchor assembly of FIG. 1A.
Figure 2:
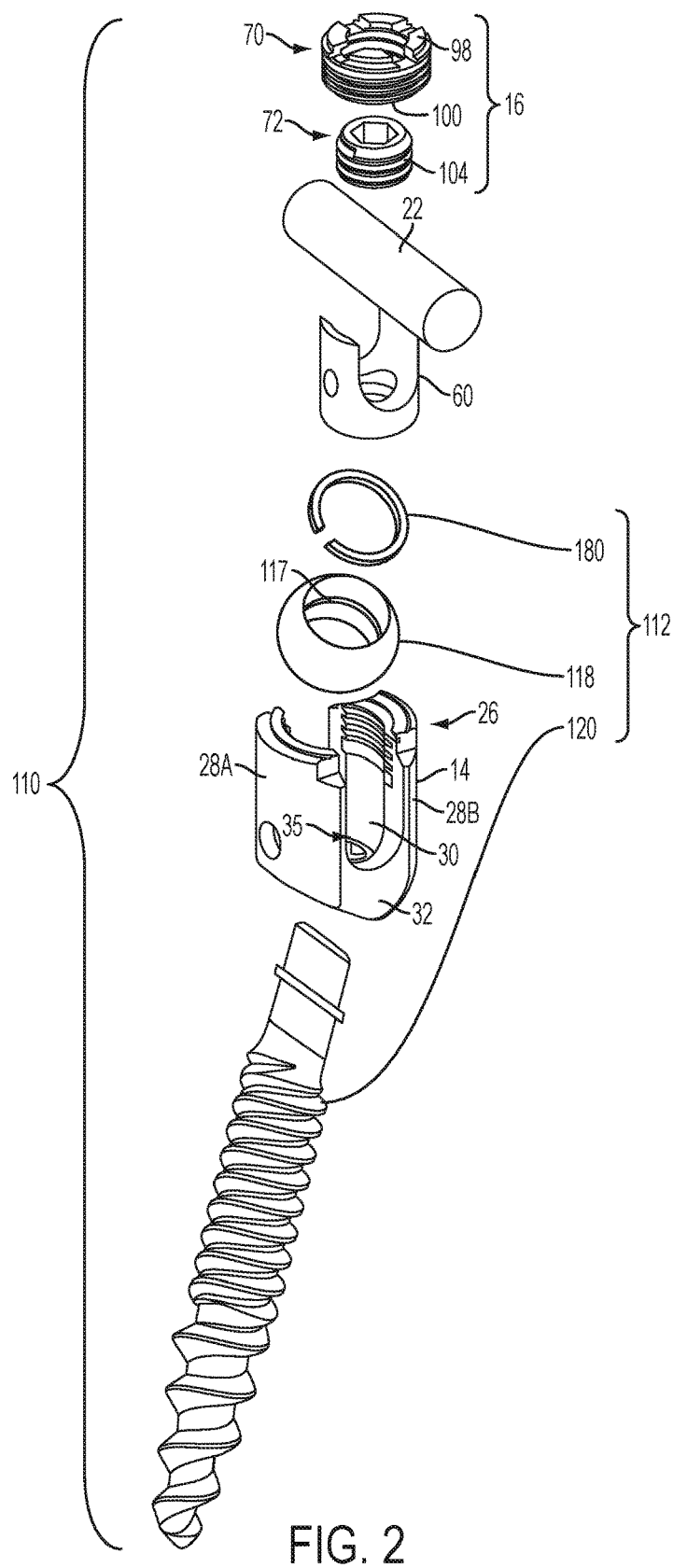
FIG. 2 is an exploded view of a bone anchor assembly including a multi-part bone anchor.

FIG. 2 illustrates a bone anchor assembly 110 that is similar to the bone anchor assembly 10 shown in FIGS. 1A and 1B, except that the bone anchor assembly 110 includes a multi-component bone anchor. As shown in FIG. 2, the bone anchor includes a shank 120 configured to engage bone, a spherical head or ball 118, and a clip 180 configured to be engaged between and to mate the ball 118 to the shank 120 in an assembled configuration. During manufacturing or during a surgical procedure, either before or after the shank 120 is implanted, the shank 120 can be proximally advanced, e.g., bottom-loaded, into the receiver member 14 and then mated to the ball 118 by the clip 180. The ball 180 can be polyaxially seated within a polyaxial seat in the receiver member 14 in a ball and socket like arrangement such that the ball 118 and the shank 120 can pivot relative to the receiver member 14. The clip 180 will lock the ball 118 to the shank 120 such that the shank 120 is mated to the receiver member 14. The shank 120 can be polyaxially moved relative to the receiver member 14, and once in a desired position a closure mechanism can be applied to the receiver member to lock a spinal fixation element, such as a spinal rod, therein and to also lock the receiver member 14 in a fixed position relative to the shank 120.

Figure 3:
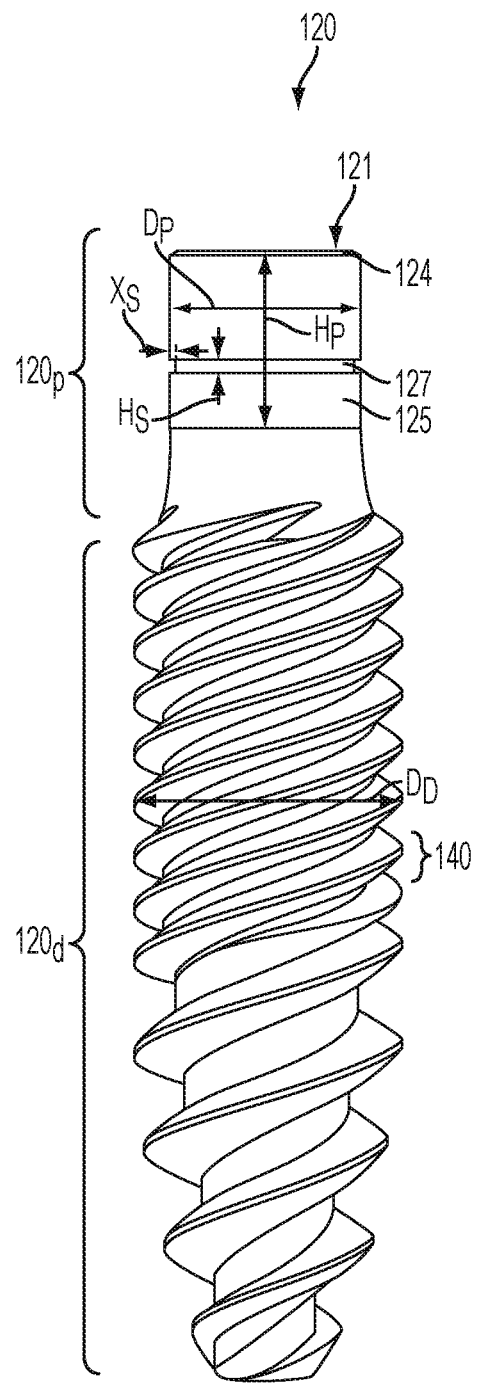
FIG. 3 is a side view of a shank of the bone anchor of FIG. 2.

The shank 120 is illustrated in more detail in FIG. 3, and as shown the elongate shank 120 includes a proximal head portion 120p and a distal portion 120d. In this embodiment, the distal bone-engaging portion 120d is in the form of a threaded shank having an external bone engaging thread 140, while the proximal portion 120p is thread-free and is in the form of a head. While the proximal portion 120p can have various shapes and sizes, in an exemplary embodiment, the proximal portion 120p is generally cylindrical and has a major diameter $D_P$ that is less than a major diameter $D_D$ of the distal portion 120d. The major diameter $D_P$ of the proximal head portion 120p of the shank 120 can be less than a diameter $D_R$ (not shown) of an opening or aperture 35 in a distal end 32 of the receiver member 14 such that the proximal head portion 120p can be received through the aperture 35. Conversely, the distal portion 120d of the shank 120 can have a major diameter $D_D$ that is greater than the diameter $D_R$ (not shown) of the aperture 35 in the distal end 32 of the receiver member 14 such that the distal portion 120d of the shank 120 is prevented from passing through the aperture 35. Such a configuration can allow the proximal portion 120p of the shank 120 to be proximally advanced through the aperture 35 in the distal end 32 of the receiver member 14, i.e., "bottom-loaded" into the receiver member 14. A person skilled in the art will appreciate, however, that the shank 120 need not have a major diameter $D_D$ that is greater than the diameter of the aperture 35 in receiver member 14, and any sized shank can be used with the present invention. As further shown in FIG. 3, the proximal portion 120p of the shank 120 can also have a substantially planar proximal surface 121 that can optionally include a tool receiving recess therein (see FIG. 6B).

As indicated above, the proximal head portion 120p of the shank 120 is configured to mate with the clip 180, which also mates to the ball 118 to thereby lock the ball 118 onto the proximal head portion 120p of the shank 120. While various features can be used to mate the clip to the head portion 120p, as shown in FIG. 3, a substantially cylindrical sidewall 125 of the proximal head portion 120p can include a first annular groove 127 formed therein to receive the clip 180. As discussed further below, in one embodiment the annular groove 127 and the clip 180 can be configured to prevent axial translation of the clip 180 with respect to the shank 120 when mated together. The groove can have a variety of configurations, but in an exemplary embodiment, the annular groove 127 is formed around the entire circumference of the shank 120 and has a constant depth $X_S$ and a constant height $H_S$. In other embodiments, as discussed below, the groove can be formed around a partial circumference of shank and/or can have varying dimensions. The location of the annular groove 127 can also vary, but it is preferably disposed at a location along the proximal head portion 120p of the shank that is configured to retain the ball 118 in a position such as that shown in FIG. 6A. In an exemplary embodiment, the annular groove 127 is located at an intermediate position between proximal and distal ends of the proximal head portion 120p.

Figure 6D:
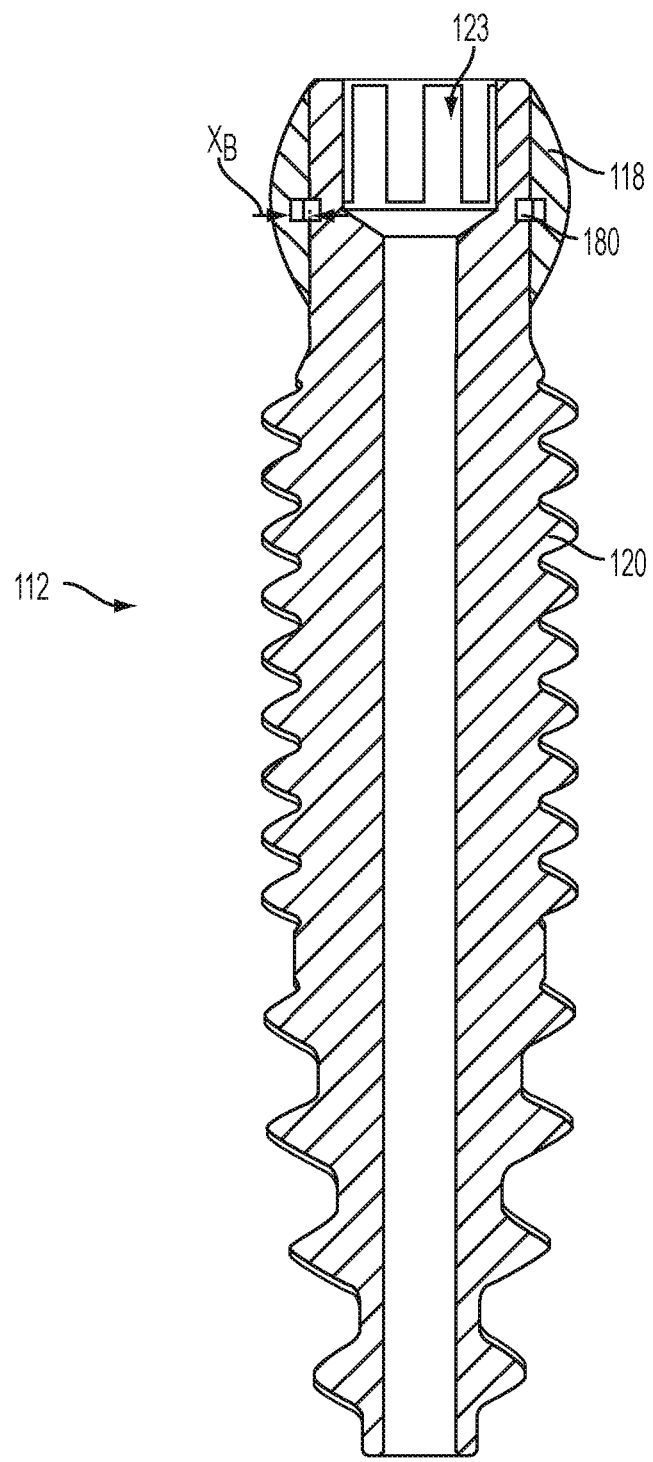
FIG. 6D is a cross-sectional view of the bone anchor of FIG. 6A.
Figure 7:
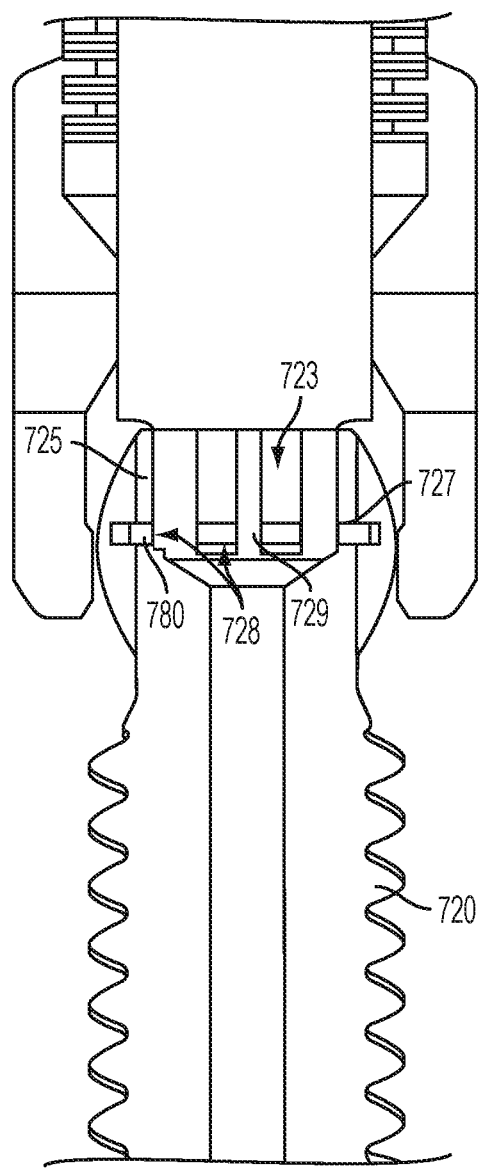
FIG. 7 is a cross-sectional view of another embodiment of a bone anchor.

As indicated above, the annular groove formed in the shank can have various configurations. For example, FIG. 7 shows another embodiment of a shank 720 that includes a groove 727 that intersects a tool receiving recess or driving interface 723. A clip 780 engaged in the groove 727 can bear against an instrument, e.g., a driving tool, in the driving interface 723 such that the shank 720 is mated to and retained on the instrument. The groove 727 can include a first portion 728 that intersects the driving interface 723 and that is configured to allow the clip 780 to bear against a tool within the driving interface. The first portion 728 can be in the form of opposed cut-outs or openings extending through the sidewall 725 of the shank (compare with FIG. 6D, in which the clip 180 does not penetrate the tool receiving recess 123). The groove 727 can also include a second portion 729 that does not penetrate the sidewall 725 of the shank 720 and that is configured to retain the clip 780 outside of the driving interface 723. The second portion 729 can likewise be formed in opposed sidewalls of the shank 720.

Returning to the embodiment of FIG. 3, the proximal head portion 120p of the shank can include various other features. For example, the head portion 120p can be configured to facilitate mating with the clip 180. As shown, the head portion 120p can include a tapered lead portion at a proximal end thereof that is configured to gradually expand the clip 180 as the clip 180 is advanced distally onto the shank 120. In an exemplary embodiment, the tapered lead portion is a substantially spherical surface 124 that extends between the proximal surface 121 and the cylindrical sidewall 125 on the proximal head portion 120p. It will be understood, however, that the tapered lead portion can have various configurations and can be either formed on the proximal head portion 120p, as shown in FIG. 3, or can be separate therefrom. For example, the tapered lead portion can be a separate member or blank (not shown) sized and shaped like the spherical surface 124 and configured to reversibly mate to the proximal head portion 120p of the shank 120 such that a clip 180 can be expanded when advanced distally on the blank and, when the blank is mated with the proximal portion 120p of the shank 120, the clip 180 can be further advanced directly onto the proximal portion 120p of the shank and the blank can be removed from the shank 120. The blank can be mated to the shank 120 using various techniques, such as threads, a twist-lock, snap-fit, pressure fit, or other mechanical engagement mechanisms.

Figure 4:
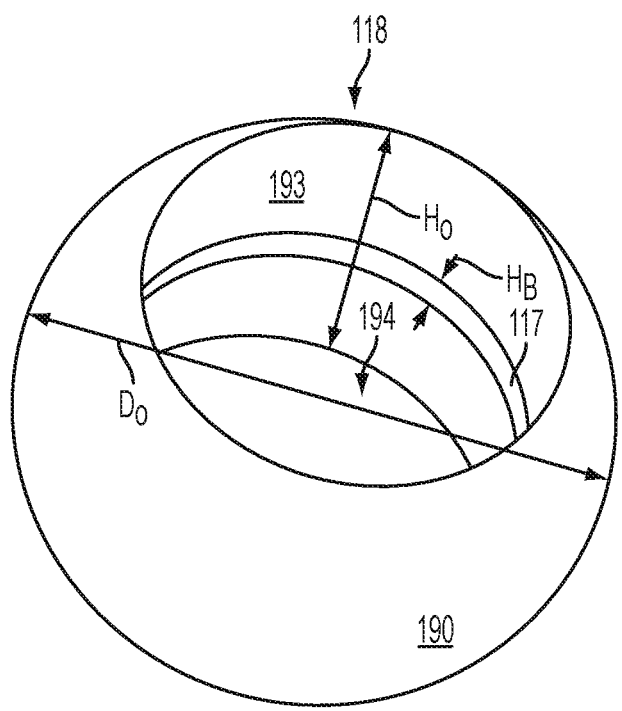
FIG. 4 is a perspective view of a ball of the bone anchor of FIG. 2.

The ball 118 of the bone anchor is shown in more detail in FIG. 4, and is configured to receive the proximal head portion 120p of the shank 120 therein with the clip 180 engaged there between. While the ball 118 can have various configurations, in an exemplary embodiment, the ball 118 is at least partially spherical to allow the ball 118 to be seated within a spherical recess in the receiver member 14 to form a ball and socket like arrangement that allows the shank 120 to pivot relative to the receiver member 14. As shown in FIG. 4, the ball 118 can be a truncated sphere with a substantially spherical exterior surface 190. While the spherical exterior surface 190 can provide for a full range of polyaxial motion, in other embodiments, the spherical outer surface 190 can include one or more flat portions (not shown) that correspond to flat portions of the receiver member 14 such that angulation of the bone anchor is limited to a single plane. When mated with the ball 118, in some embodiments, the spherical surface 124 of the shank and the spherical exterior surface 190 of the ball 118 can form a substantially continuous spherical surface (see FIG. 6A). However, in other embodiments, the spherical surface 124 of the shank 120 and the spherical exterior surface 190 of the ball 118 can share a common center point and can form an interrupted spherical surface.

The dimensions of the ball can also vary, but in an exemplary embodiment, the ball 118 can have a diameter $D_O$ that is greater than the diameter $D_R$ (not shown) of the aperture 35 in the distal end 32 of the receiver member 14 such that the ball 118 is prevented from passing through the aperture 35. The ball 118 can have a height Ho that is less than or equal to a height $H_P$ of the proximal head portion 120p of the shank 120. In the illustrated embodiment, the ball 118 is rigid and inflexible. For example, the ball 118 can be non-expandable so as to prevent the outer ring from deforming and detaching from the shank 120 when the bone anchor is coupled to the receiver member 14. In particular, the ball 118 can be solid with an unbroken circumference, having no slits or cuts formed therein such that it does not bend, compress, or expand.

As further shown in FIG. 4, the ball 118 can include an inner surface 193 that defines a lumen or bore 194 extending therethrough that is configured to receive the proximal portion 120p of the shank 120. In an exemplary embodiment, the bore 194 is cylindrical to correspond with the proximal head portion 120p of the shank 120 (see FIG. 6D), however, it will be understood that the bore can have various other shapes, such as hourglass or frustoconical, for example.

In order to facilitate mating engagement between the ball 118 and the clip 180, the inner surface 193 of the bore 194 of the ball 118 can include a second annular groove 117 formed therein for seating at least a portion of the clip 180. Similar to the first annular groove 127, the second annular groove can have a variety of configurations, but in an exemplary embodiment, the annular groove 117 is formed around the entire circumference of the bore 194 and has a constant depth (not shown) and a constant height $H_B$. In other embodiments, as discussed below, the groove 117 can be formed around a partial circumference of bore in the ball 118 and/or can have varying dimensions. The location of the annular groove 117 can also vary, but it is preferably disposed at a location along the length of the bore that is configured to retain the ball 118 on the shank 120 in a position such as that shown in FIG. 6A. In an exemplary embodiment, the annular groove 117 is located at an intermediate position between proximal and distal ends of the bore 194 in the ball 118.

Figure 5A:
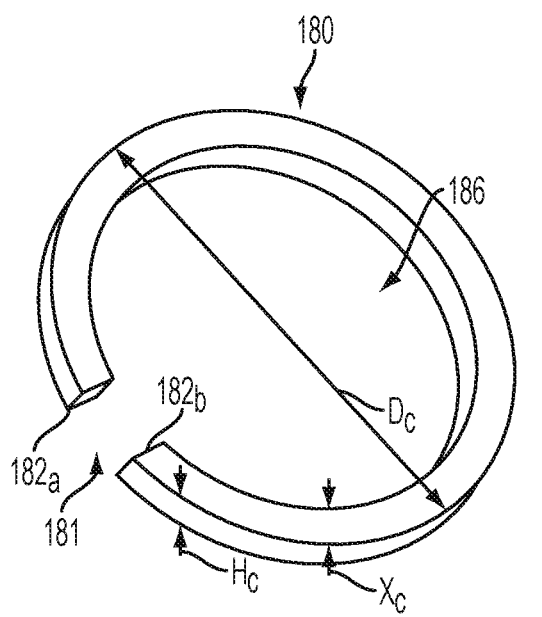
FIG. 5A is a perspective view of a clip of the bone anchor of FIG. 2.

The clip 180 is illustrated in more detail in FIG. 5A and can generally be circular or cylindrical. The clip 180 can be configured to be partially seated within the first annular groove 127 of the shank 120 and partially seated within the second annular groove 117 of the ball 118 to mate the shank 120 with the ball 118. In an exemplary embodiment, the clip 180 is C-shaped with a radial slit 181 for allowing a diameter $D_C$ of the clip to be adjusted. The clip 180 can have a height $H_C$ that is less than or equal to a height $H_S$ of the first annular groove 127 and less than or equal to a height $H_B$ of the second annular groove 117. In an exemplary embodiment, the height $H_C$ of the clip is substantially equal to each of the height $H_S$ of the first annular groove 127 and the height $H_B$ of the second annular groove 117 such that, when the clip 180 is partially seated within the first and second annular grooves 127, 117 to mate the shank 120 and the ball 118, the ball 118 and the shank 120 are prevented from translating axially relative to one another. The clip 180 can also have a width $X_C$ that is less than each of a depth $X_S$ of the first annular groove 127 and a depth $X_B$ of the second annular groove 117, and that is equal to or less than a combined depth $X_S$ of the first annular groove 127 and depth $X_B$ of the second annular groove such that the clip 180 can be entirely recessed within both grooves. In an exemplary embodiment, the clip 180 has a width $X_C$ that is less than the combined depth $X_S$ of the first annular groove 127 and depth $X_B$ of the second annular groove 117 so as to allow the clip 180 to expand or contract into one of the grooves 117, 127 as the shank and ball are advanced relative to one another. While FIG. 5A illustrates a C-shaped clip, it will be understood that the clip can have various other configurations, such as an E-clip, a K-type clip, a wire, band, tube, or ring without a slit, as discussed further below, etc.

Figure 5B:
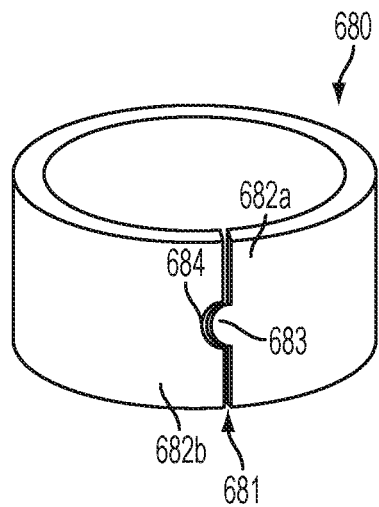
FIG. 5B is a perspective view of another embodiment of a clip.

As indicated above, the slit 181 in the clip 180 can allow the clip to expand and contract such that a maximum diameter $D_C$ of the clip 180 is adjustable, i.e., can increase or decrease. For example, the maximum diameter $D_C$ can increase when the proximal head portion 120p of the shank 120 is being advanced through a lumen 186 of the clip 180, or the diameter $D_C$ can decrease when the clip 180 is being advanced through the lumen 194 of the ball 118. The slit can have a variety of configurations. For example, as shown in FIG. 5A, the slit 181 can be in the form of a radial cut extending longitudinally through the clip 180 from an outer surface 187 to an inner surface 188 thereof. In an exemplary embodiment, the slit 181 defines straight opposed first and second sides 182a, 182b. In other embodiments, the slit can be non-linear, interlocking or non-interlocking. For example, FIG. 5B, shows another embodiment of a clip 680 that has a non-linear slit 681 that defines a first side 682a with a tab 683 formed thereon and a second side 682b with a complementary recess 684 formed therein such that the tab 683 and the recess 684 are configured to interlock the first and second sides 682a, 682b. The slit can vary in size and a distance between first and second sides 182a, 182b of the slit can increase or decrease as the ring 180 expands or contracts.

Figure 5C:
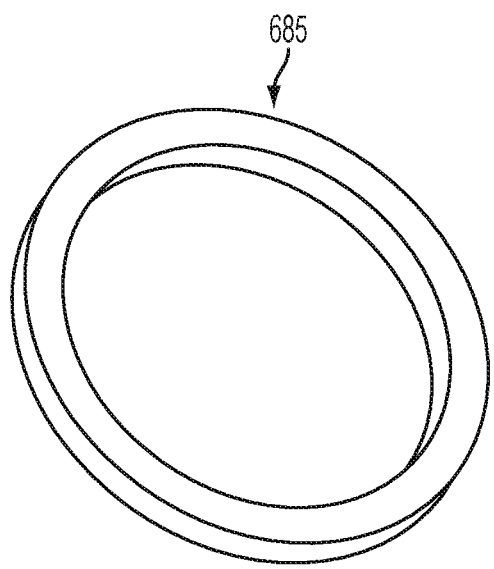
FIG. 5C is a perspective view of another embodiment of a clip.

As indicated above, in another embodiment, the clip can be slit-free while still being flexible to allow the diameter to increase and decrease. By way of example, FIG. 5C illustrates a clip 685 in the form of a continuous ring or band having an uninterrupted circumference, i.e., without a slit, that can expand and contract. The clip can be formed from an expandable material such that a maximum diameter of the clip can increase and/or decrease when a force is applied thereto. Exemplary materials include, by way of non-limiting example, shape memory alloys, such as nitinol, and any material that has elastic properties. In another aspect, the clip can heated and/or cooled such that a maximum diameter of the clip can be adjusted.

Figure 6A:
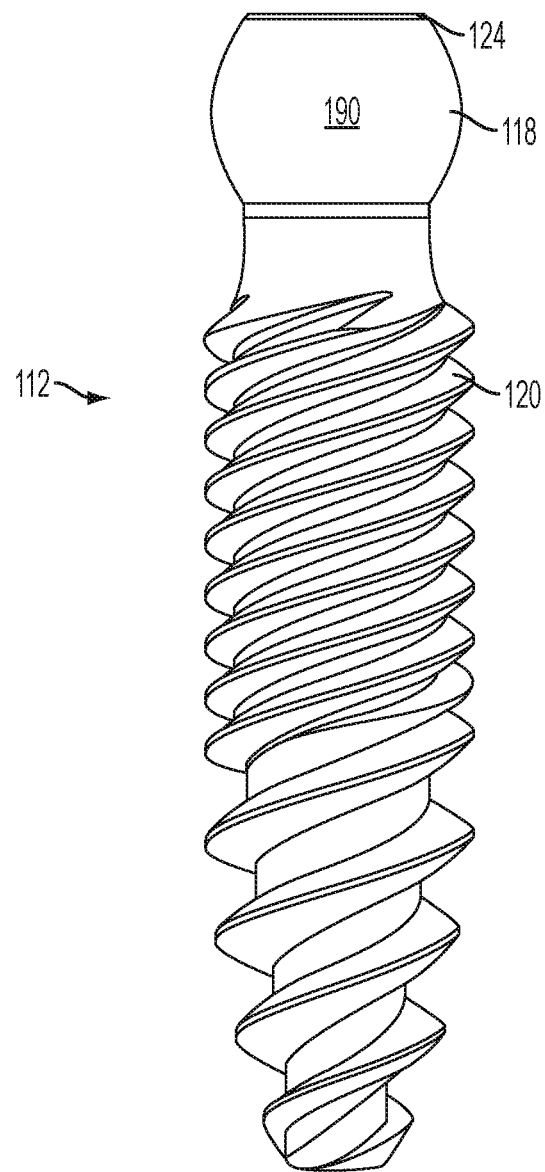
FIG. 6A is a side view of the multi-part bone anchor of FIG. 2 shown fully assembled.
Figure 6B:
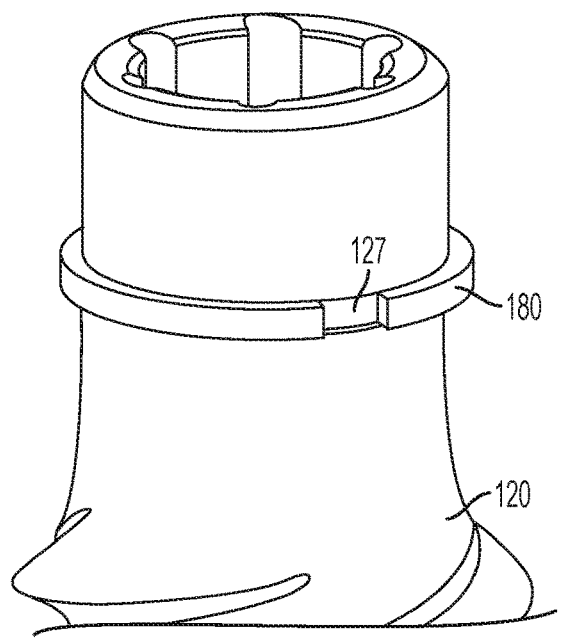
FIG. 6B is a perspective view of the clip of FIG. 5A engaged with the shank of FIG. 3.
Figure 6C:
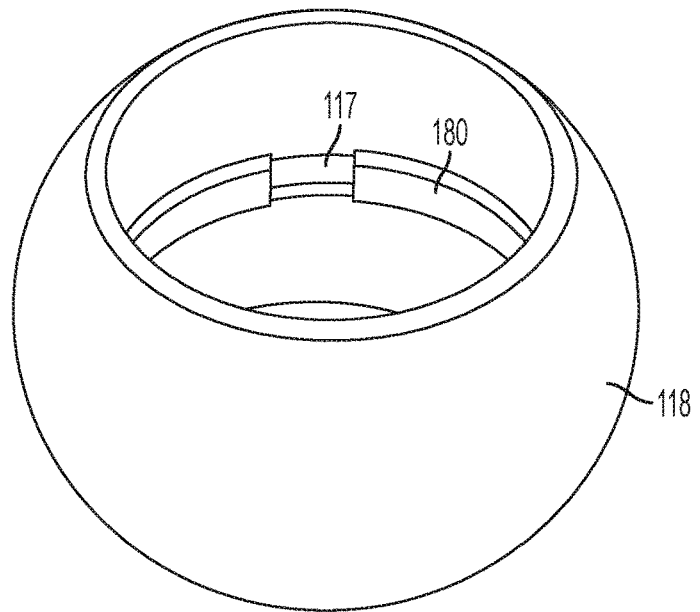
FIG. 6C is a perspective view of the clip of FIG. 5A engaged with the ball of FIG. 4.

In use, the bone anchor assembly 110 can be assembled during manufacturing, before surgery, or intraoperatively. FIGS. 6A and 6D show an exemplary assembled bone anchor. While the method is shown in connection with the bone anchor assembly of FIG. 2, the method can be used with any of the bone anchor assemblies disclosed herein. The proximal portion 120p of the shank 120 can be proximally advanced through the aperture 35 in the distal end 32 of the receiver member 14, i.e., bottom-loaded into the receiver member 14, and the ball 118 can be top-loaded into the receiver member 14 thereafter. The clip 180 can initially be seated in one of the annular groove 127 in the shank 120 (as shown in FIG. 6B) and the annular groove 117 in the ball (as shown in FIG. 6C).

In one embodiment, the clip 180 can be initially seated in the annular groove 127 in the shank 120. In this embodiment, the clip 180 can have a width $X_C$ that is equal to a depth $X_S$ of the first annular groove 127. During assembly, the diameter $D_C$ of the clip 180 can be expanded, e.g., increased, to receive the proximal head portion 120p of the shank 120 within the lumen 186 thereof. For example, the clip 180 can be expanded over a tapered lead, e.g., a spherical surface 124 formed at a proximal end of the proximal head portion 120p of the shaft 120 or, alternatively, the clip 180 can be expanded over a tapered blank, which can then be displaced by the proximal head portion 120p of the shank 120 when the clip 180 is sufficiently expanded. Once the clip 180 is aligned with the groove 127, the clip can return to its original state to be seated within the annular groove 127. As the proximal head portion 120p of the shank 120 is advanced through the bore 194 of the ball 118, the depth $X_S$ of the first annular groove 127 can allow the clip to compress and be fully received within the annular groove 127. Once the first annular groove 127 is aligned with the second annular groove 117 in the ball 118, the clip 180 can once again return to its original state such that the clip 180 extends partially into each groove 117, 127.

In another embodiment, the clip 180 can be initially seated in the annular groove 117 in the ball 118. In this embodiment, the clip 180 can have a width $X_C$ that is equal to a depth $X_B$ of the second annular groove 117. During assembly, the diameter $D_C$ of the clip 180 can be compressed, e.g., decreased, as the clip 180 is advanced through the lumen 194 of the ball 118. Once the clip 180 is aligned with the groove 117, the clip can return to its original state to be seated within the annular groove 117. As the proximal head portion 120p of the shank 120 is advanced through the bore 194 of the ball 118, the depth $X_B$ of the second annular groove 117 can allow the clip to expand and be fully received within the annular groove 117. Once the first annular groove 127 is aligned with the second annular groove 117 in the ball 118, the clip 180 can once again return to its original state such that the clip 180 extends partially into each groove 117, 127.

With the grooves 117, 127 are aligned and the clip 180 extending into each of the grooves 117, 127, the shank 120 and the ball 118 will be locked a substantially fixed relationship relative to each other, as shown in FIG. 6D. Since the ball 118 is sized to prevent passage through the aperture 35 of the receiver member 14, the proximal portion 120p of the shank 120 is maintained within the receiver member 14. The multi-component bone anchor thus allows for assembly using a bottom loading technique. This can be particularly advantageous with large diameter shanks that are not sized to be distally advanced through the proximal end of the receiver and through the aperture in the receiver member. The secure mating connection between the components also allows the ball 118 to be sized so as to prevent passage through the aperture 35 in the receiver member 14, even when the shank 120 is fully angled to the maximum angulation allowed for the illustrated favored-angle bone anchor assembly.

The bone anchor 120 can be implanted in bone, either before or after coupling the receiver member 14 to the shank 120, using a driver tool fitted with the bone anchor. In some embodiments, as discussed with respect to FIGS. 7A and 7B, the clip 180 can intersect the driving interface 723 and can bear against the driver tool to retain shank on the driving tool. A compression member, if utilized, can be positioned within the receiver member 14 such that the arms 62A, 62B of the compression member 60 are aligned with the arms 28A, 28B of the receiver member 14 and the distal-facing surface of the compression member 60 is in contact with the bone anchor. The compression member 60 can exert a frictional force on part of the bone anchor, e.g., the ball 118, to maintain the shank 120 in a desired orientation relative to the receiver member 14, while still allowing movement of the shank 120 with respect to the receiver member 14.

Once the bone anchor is implanted in bone and the receiver member 14 is attached thereto, the receiver member 14 can be pivoted or angulated relative to the bone anchor. One or more bone anchor assemblies (not shown) can also be deployed into bone using the same or different techniques. A spinal fixation element, e.g. the spinal rod 22, can be positioned in the recess 30 of the receiver member 14 and can be manipulated in various ways using various tools so that the spinal rod 22 extends through one or more bone anchor assemblies. Manipulating the spinal rod 22 can change an angle of the receiver member 14 relative to the bone anchor. When the spinal rod 22 is in a desired position, a closure mechanism 16 can be engaged with the inner thread provided on the arms 28A, 28B of the receiver member 14. The closure mechanism 16 can fix the spinal rod 22 relative to the bone anchor assembly 110, and also cause the compression member 60 to engage the part of the bone anchor, e.g., the ball 118, to lock the receiver member 14 in a fixed position relative to the shank 120.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A bone anchor assembly, comprising:
   a single piece shank having a distal threaded portion and a proximal head portion;
   a tool receiving recess formed in the proximal head portion of the shank;
   a groove formed in the proximal head portion that intersects the tool receiving recess; and
   a clip configured to be disposed within the groove such that the clip bears against a driving tool in the tool receiving recess to retain the shank on the driving tool.

2. The bone anchor assembly of claim 1, wherein the groove includes a first portion that intersects the tool receiving recess to allow the clip to bear against the driving tool within the tool receiving recess and a second portion that does not penetrate the tool receiving recess to retain the clip outside of the tool receiving recess.

3. The bone anchor assembly of claim 2, wherein the first portion of the groove is formed as opposed openings extending through the sidewall of the shank.

4. The bone anchor assembly of claim 3, wherein the second portion of the groove is formed as opposed sidewalls of the shank that are not penetrated by the groove.

5. The bone anchor assembly of claim 1, further comprising:
   a ball having a spherical exterior surface and a central lumen sized to receive the proximal head portion of the shank;
   wherein the central lumen includes an annular groove formed therein, and wherein the clip is configured to extend into the annular groove to lock the ball in engagement with the shank.

6. The bone anchor assembly of claim 5, further comprising:
   a receiver member having an aperture formed in a distal end thereof sized such that the proximal head portion of the shank can pass through the aperture and such that the ball cannot pass through the aperture.

7. The bone anchor assembly of claim 6, wherein a major diameter of the distal threaded portion of the shank is greater than a diameter of the aperture formed in the receiver member.

8. The bone anchor assembly of claim 5, wherein the proximal head portion of the shank and the central lumen of the ball are cylindrical.

9. The bone anchor assembly of claim 1, wherein the clip comprises a circlip.

10. The bone anchor assembly of claim 1, wherein the clip comprises a C-shaped band having a radial cut formed therein, a first side of the radial cut having a tab configured to interlock with a complementary recess formed in a second side of the radial cut.

11. The bone anchor assembly of claim 1, wherein the clip is a continuous ring formed from an expandable material.

12. The bone anchor assembly of claim 1, wherein the proximal head portion of the shank tapers towards its proximal end to provide a lead-in surface for expanding the clip as the clip is slid distally over the head portion and into the first groove during assembly.

13. A method of assembling a bone anchor assembly, comprising:
   engaging a clip with a groove formed in a proximal head portion of a single piece shank, wherein the groove intersects a tool receiving recess formed in the proximal head portion; and
   inserting a driving tool into the tool receiving recess until the clip bears against the driving tool to retain the shank on the driving tool.

14. The method of claim 13, further comprising expanding the clip over a tapered lead formed at a proximal end of the proximal head portion of the shank.

15. The method of claim 13, further comprising:
advancing the proximal head portion of the shank proximally through an aperture formed in a distal end of a receiver member; and
advancing the proximal head portion of the shank into a central lumen of a ball having a spherical exterior surface until the clip engages an annular groove formed in the central lumen to lock the ball in engagement with the shank.

16. The method of claim 15, further comprising positioning the ball in a seat portion of the receiver member.

17. The method of claim 16, further comprising implanting a threaded distal portion of the shank in bone and polyaxially moving the receiver member relative to the shank.

18. The method of claim 17, further comprising positioning a spinal fixation element within the receiver member and applying a closure mechanism to the receiver member to lock the receiver member in a fixed position relative to the shank.

19. The method of claim 16, wherein the ball is inserted into a proximal end of the receiver member.

\* \* \* \* \*